(12) United States Patent
Cao et al.

(10) Patent No.: US 12,011,189 B2
(45) Date of Patent: Jun. 18, 2024

(54) FLUID FLOW METAL SLEEVE

(71) Applicant: BEIJING SMTP TECHNOLOGY CO., LTD., Beijing (CN)

(72) Inventors: Qun Cao, Beijing (CN); Zhen Feng, Beijing (CN)

(73) Assignee: BEIJING SMTP TECHNOLOGY CO., LTD., Beijing (CN)

( * ) Notice: Subject to any disclaimer, the term of this patent is extended or adjusted under 35 U.S.C. 154(b) by 626 days.

(21) Appl. No.: 17/270,343

(22) PCT Filed: Jul. 8, 2019

(86) PCT No.: PCT/CN2019/095058
§ 371 (c)(1),
(2) Date: Feb. 22, 2021

(87) PCT Pub. No.: WO2019/228544
PCT Pub. Date: Dec. 5, 2019

(65) Prior Publication Data
US 2021/0307778 A1    Oct. 7, 2021

(30) Foreign Application Priority Data
Aug. 24, 2018    (CN) .......................... 201821373518.X (51) Int. Cl.
*A61B 17/32*    (2006.01)
*A61M 39/10*    (2006.01)

(52) U.S. Cl.
CPC ..... *A61B 17/320068* (2013.01); *A61M 39/10* (2013.01); *A61B 2017/320084* (2013.01); *A61M 2205/42* (2013.01)

(58) Field of Classification Search
CPC .......... A61B 17/320068; A61B 2017/320084; A61B 2017/32007; A61B 17/32006;
(Continued)

(56) References Cited

U.S. PATENT DOCUMENTS 4,808,154 A * 2/1989 Freeman ............. A61F 9/00745
604/22
4,816,017 A   3/1989 Hood et al.
(Continued)

FOREIGN PATENT DOCUMENTS

CN    101772325 A    7/2010
CN    102711643 A    10/2012
(Continued)

OTHER PUBLICATIONS

1 Extended European Search Report issued in European Application No. 19811537.0, dated Aug. 16, 2021 (6 pages).
(Continued)

*Primary Examiner* — Katherine H Schwiker
*Assistant Examiner* — Zehra Jaffri
(74) *Attorney, Agent, or Firm* — Osha Bergman Watanabe & Burton LLP (57) ABSTRACT

A fluid flow metal sleeve includes a sleeve main body and an elongation portion, which are of a hollow structure as a whole. The sleeve main body is connected to the elongation portion in a threaded manner, and a terminal end of the sleeve main body is connected to an ultrasound scalpel handle and enables an ultrasound scalpel to pass therethrough. The fluid flow metal sleeve can control the direction of fluid flow during incision with the ultrasound scalpel so as to achieve the lubricating and cooling effects on a scalpel head. In addition, due to the use of a metal structure, a user can extend an original holding part from an outer portion of the ultrasound scalpel handle to an outer wall of the metal sleeve as required. The fluid flow metal sleeve also has an adjustable telescopic function so as to be adapted to different application scenarios, and limits the length of extension of the scalpel head so as to limit the depth during incision to improve the safety of surgery.

11 Claims, 6 Drawing Sheets

(58) Field of Classification Search
CPC .... A61B 2017/32006; A61B 17/32007; A61B 17/32008; A61B 2017/32008; A61B 17/32009; A61B 2017/32009; A61M 39/10; A61M 2205/42
See application file for complete search history.

(56) References Cited

U.S. PATENT DOCUMENTS

| | | |
|---|---|---|
| 5,195,952 A | 3/1993 | Solnit et al. |
| 5,346,502 A | 9/1994 | Estabrook et al. |
| 5,984,904 A | 11/1999 | Steen et al. |
| 6,177,755 B1 | 1/2001 | Hur |
| 2010/0160851 A1* | 6/2010 | Dimalanta .......... A61F 9/00736 604/22 |
| 2011/0092888 A1 | 4/2011 | Gerg |
| 2024/0023989 A1* | 1/2024 | White ................ A61B 1/00128 |

FOREIGN PATENT DOCUMENTS

| | | | |
|---|---|---|---|
| CN | 105939680 A | 9/2016 | |
| WO | WO-2015069445 A1 * | 5/2015 | ............... A61F 2/16 |

OTHER PUBLICATIONS

International Search Report issued in PCT/CN2019/095058 mailed on Sep. 30, 2019 (3 pages).
Written Opinion of the International Searching Authority issued in PCT/CN2019/095058 mailed on Sep. 30, 2019 (3 pages).
Office Action in counterpart Australian Patent Application No. 2019275767 issued on Mar. 24, 2021 (9 pages).

* cited by examiner

FLUID FLOW METAL SLEEVE

CROSS-REFERENCE TO RELATED APPLICATIONS

This application is a U.S. National Stage of International Application No. PCT/CN2019/095058, filed on Jul. 8, 2019, which claims the benefit of Chinese Patent Application No. 201821373518.X, titled "METAL LIQUID FLOW SLEEVE" filed on Aug. 24, 2018. The contents of the applications are hereby incorporated by reference in their entireties for all purposes.

TECHNICAL FIELD

The present disclosure relates to the field of medical devices, in particular to a medical pipeline device, and especially to a fluid flow metal sleeve.

BACKGROUND

In modern clinical medical operations, ultrasound surgical devices have been gradually applied in various fields such as orthopedics, neurosurgery, burns, and ophthalmology. An ultrasound surgical device will have friction on body tissues during an operation and then generate heat. In some applications of surgery, the heat generated by friction may have a positive therapeutic effect, such as hemostatic treatment on a body tissue that is incised, but in most cases, the heat generated by friction will damage cells and tissues, causing postoperative complications to have adverse effects. Therefore, when an ultrasound surgical device is used for surgery, it is generally equipped with a fluid flow system for cooling the friction hot point of the scalpel head by means of a fluid flow sleeve.

Most of the fluid flow sleeves in the prior art are made of polymer materials, and cannot achieve repeated disinfection and reuse, thus having poor environmental protection performance. The sleeve has does not have a part that can be held by the user during the incision, which is easy to cause scald in an improper use. In addition, none of the fluid flow sleeves in the prior art has a length adjustment function and has a tool depth restriction function during the incision, resulting in high risk of injury by incision.

SUMMARY

In view of the existing problems, the present disclosure provides a fluid flow metal sleeve, comprising a sleeve main body and an elongation portion, which are of a hollow structure as a whole. The sleeve main body is connected to the elongation portion in a threaded manner, a terminal end of the sleeve main body is connected to an ultrasound scalpel handle and enables the ultrasound scalpel to pass therethrough, and the surfaces of the sleeve main body and the elongation portion are provided with noise reduction notches. The noise reduction notches are configured to reduce noise from the fluid flow metal sleeve.

In the fluid flow metal sleeve of the present disclosure, preferably, the elongation portion has two or more stages.

In the fluid flow metal sleeve of the present disclosure, preferably, a front end of the head of the elongation portion and the sleeve main body are provided with slip-proof notches, and an outer side of the elongation portion is provided with scale lines.

In the fluid flow metal sleeve of the present disclosure, preferably, the slip-proof notches are arc-shaped recessed notches, rectangular recessed notches, rectangular raised notches, or of other irregular shapes.

In the fluid flow metal sleeve of the present disclosure, preferably, the slip-proof notches are uniformly distributed.

In the fluid flow metal sleeve of the present disclosure, preferably, the inside of the elongation portion is provided with a limiting structure to prevent slippage of the elongation portion from the sleeve main body.

In the fluid flow metal sleeve of the present disclosure, preferably, the inside of the elongation portion with two or more stages is provided with a limiting structure to prevent slippage of each stage of the elongation portion from the elongation portion.

In the fluid flow metal sleeve of the present disclosure, preferably, the sleeve main body and the handle of ultrasound scalpel are connected by means of a threaded structure, a snap-fitting, a top thread structure, an elastic expansion structure, a plugging structure, or a clamp slot structure.

In the fluid flow metal sleeve of the present disclosure, preferably, the noise reduction notches are rectangular, circular, elliptical, or of an irregular shape.

In the fluid flow metal sleeve of the present disclosure, preferably, the noise reduction notches are of a through structure.

In the fluid flow metal sleeve of the present disclosure, preferably, the noise reduction notches are uniformly distributed.

In the fluid flow metal sleeve of the present disclosure, preferably, the threaded structure has a cross-section in the shape of a rectangle, trapezoid or triangle.

The fluid flow metal sleeve involved in the present disclosure can control the direction of fluid flow during incision with an ultrasound scalpel so as to achieve the lubricating and cooling effects on the scalpel head. The material thereof is medical-grade metal, which is not only environmentally friendly, but also achieves repeated disinfection and use. Also, a structure of one-stage or multi-stage elongation portion is used to achieve the adjustable length and improve the operability. By means of the adjustment, the scalpel head realizes the functions of performing incision and limiting the depth of exposure (cooperating with instruments such as an endoscope). The inside of the elongation portion is provided with a limiting structure, such that each stage of elongation portion has a safety limit on the limit travel so as to prevent slippage during use, such that the device has high safety in use. The front end of the elongation portion and the sleeve main body are provided with slip-proof notches of various shapes, improving the operability on length adjustment and holding. In addition, the arrangement of the noise reduction notches can effectively reduce the noise decibels during incision, and at the same time can further reduce the weight of the fluid flow metal sleeve.

The water injection sleeve of the present disclosure has a simple structure, is convenient and durable, has low a machining cost, is flexible in operation, and can be used in different forms according to surgical needs.

BRIEF DESCRIPTION OF THE DRAWINGS

To describe the technical solutions in the particular embodiments of the present disclosure more clearly, the drawings that need to be used in the description of the particular embodiments will be briefly introduced below.

DETAILED DESCRIPTION OF EMBODIMENTS

The technical solutions in the present disclosure will be described clearly and completely below with reference to the drawings. Obviously, the described embodiments are some of, rather than all of, the embodiments of the present disclosure. Based on the embodiments of the present disclosure, all other embodiments obtained by those of ordinary skill in the art without involving any inventive effort fall within the scope of protection of the present disclosure.

In the description of the present disclosure, it should be noted that orientations or position relationships indicated by terms such as "center", "upper", "lower", "left", "right", "vertical", "horizontal", "inside" and "outside" are based on orientations or position relationships shown in the drawings, which is only for convenience of describing the present disclosure and simplifying the description, rather than indicates or implies that devices or elements referred to must have a specific orientation or be constructed and operated in the specific orientation, and therefore cannot be construed as limiting the present disclosure. Furthermore, the terms "first", "second" and "third" are used for descriptive purposes only and should not be construed as indicating or implying the relative importance.

In the description of the present disclosure, it should be noted that the terms "mounting", "connecting" and "connection" should be understood in a broad sense, unless otherwise explicitly specified or defined, for example, it may be a fixed connection, a detachable connection or an integrated connection; may be a mechanical connection or an electrical connection; and may be a direct connection or an indirect connection through an intermediate medium, or may be a communication between the interior of two elements. For those of ordinary skill in the art, the specific meanings of the terms mentioned above in the present disclosure should be construed according to specific circumstances.

Figure 1:
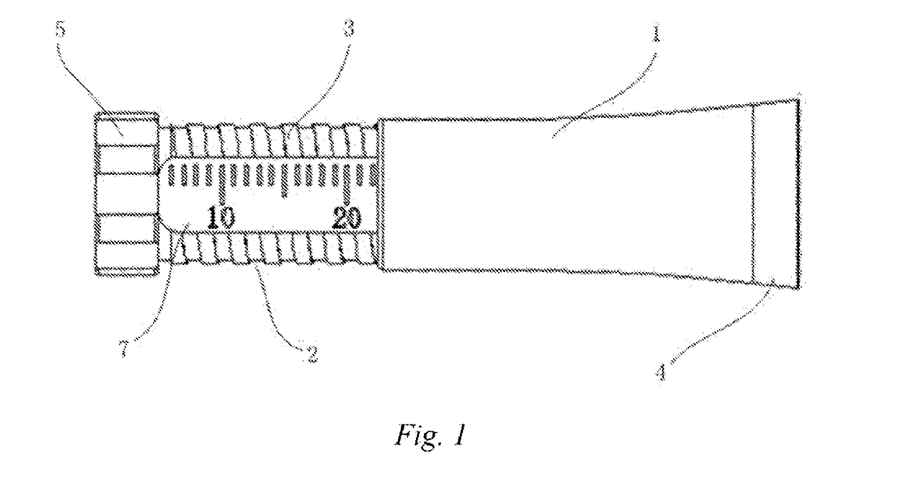
FIG. 1 is a perspective structural schematic diagram of a fluid flow metal sleeve involved in a first embodiment of the present disclosure.
Figure 2:
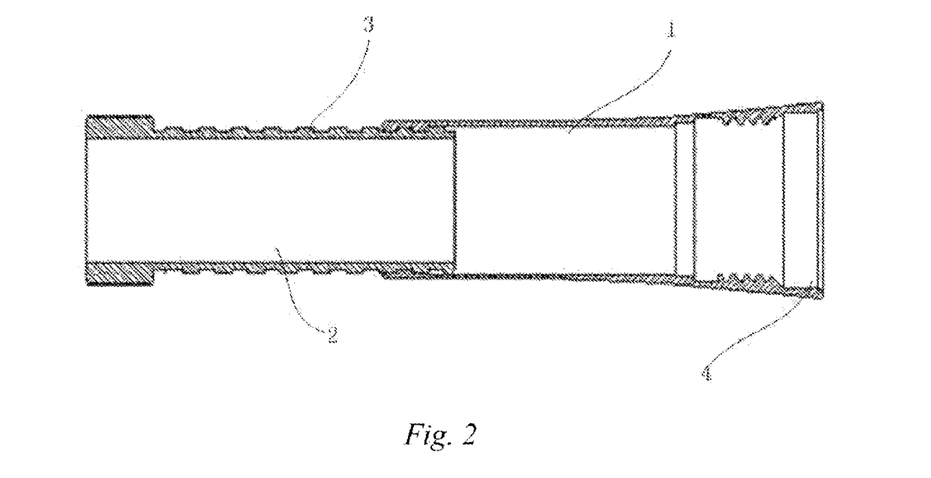
FIG. 2 is a cross-sectional structural schematic diagram of the fluid flow metal sleeve involved in the first embodiment of the present disclosure.

The present disclosure will be further described in detail below by way of the particular embodiments and with reference to the accompanying drawings. FIG. 1 is a perspective structural schematic diagram of a fluid flow metal sleeve involved in a first embodiment of the present disclosure. FIG. 2 is a cross-sectional structural schematic diagram of the fluid flow metal sleeve involved in the first embodiment of the present disclosure. As shown in FIGS. 1 and 2, the fluid flow metal sleeve involved in the first embodiment of the present disclosure comprises a sleeve main body 1 and an elongation portion 2. The sleeve main body 1 and the elongation portion 2 are connected to each other by means of a threaded structure 3, having a hollow structure as a whole. The elongation portion 2 can be retracted into the sleeve main body 1. The threaded structure may have a cross-section in the shape of a triangle, trapezoid, rectangle, etc. During use, the elongation portion 2 can be extended from the sleeve main body 1 by a certain length through the threaded structure 3 according to actual needs. In this embodiment, an outer side of the elongation portion 2 is provided with scale lines 7, by which the length of elongation of the elongation portion 2 can be adjusted, and at the same time the length of elongation can be read visually. A terminal end 4 of the sleeve main body is connected to an ultrasound scalpel handle and enables the ultrasound scalpel to pass therethrough. The sleeve main body and the ultrasound scalpel handle can be connected by means of a threaded structure, a snap-fitting structure, a top thread structure, an elastic expansion structure, a plugging structure, a clamp slot structure, etc. The threaded structure may be in various forms, such as single-head, multi-head, etc., and may have a cross-section in the shape of a triangle, trapezoid, rectangle, etc. The periphery of the front end of the head of the elongation portion 2 is provided with elongation portion slip-proof notches 5 of a tooth-like structure. The elongation portion slip-proof notches 5 may be arc-shaped recessed notches, rectangular recessed notches, rectangular raised notches, or of other irregular shapes. The elongation portion slip-proof notches 5 may be in a uniform or non-uniform distribution. The fluid flow metal sleeve involved in the first embodiment of the present disclosure uses a metal structure, the original holding part can extend from the outside of the ultrasound handle to the outer wall of the metal sleeve, and the overall sleeve has an adjustable telescopic function, achieving the adaption to different application scenarios.

Figure 3A:
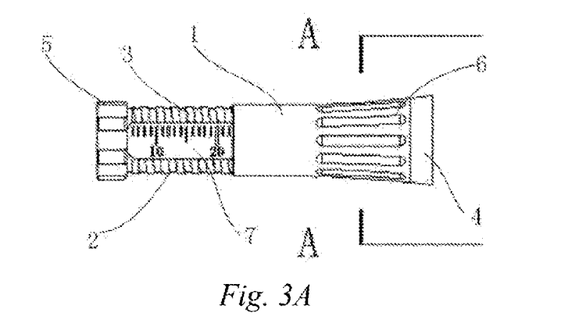
FIGS. 3A, 3B and 3C are respectively a perspective structural schematic diagram, a cross-sectional view of a front end of an elongation portion, and a cross-sectional view along AA of an example of a fluid flow metal sleeve involved in a second embodiment of the present disclosure.
Figure 3B:
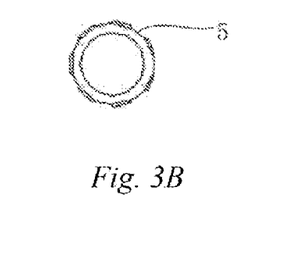
Figure 3C:
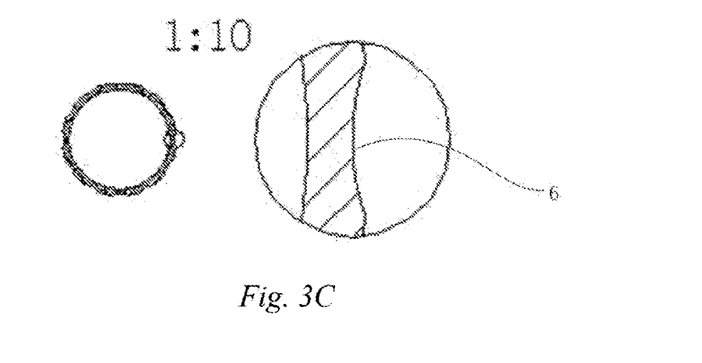
Figure 4A:
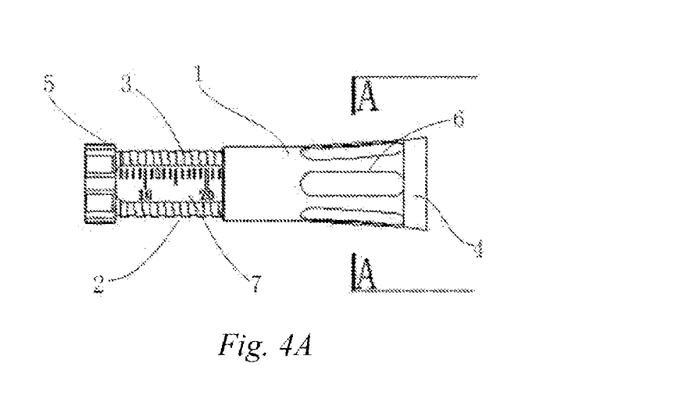
FIGS. 4A, 4B and 4C are respectively a perspective structural schematic diagram, a cross-sectional view of a front end of an elongation portion, and a cross-sectional view along AA of another example of the fluid flow metal sleeve involved in the second embodiment of the present disclosure.
Figure 4B:
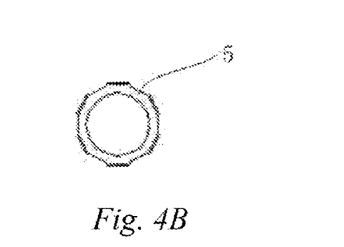
Figure 4C:
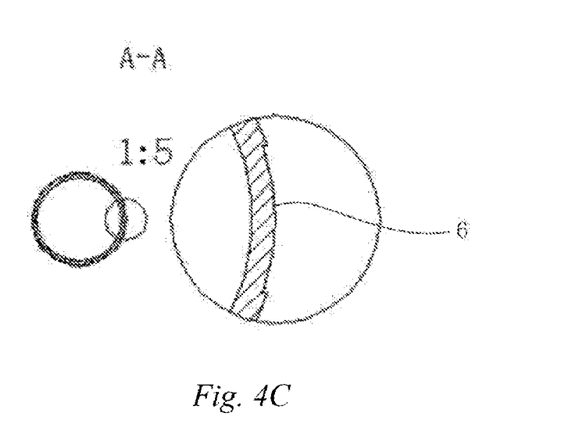
Figure 5A:
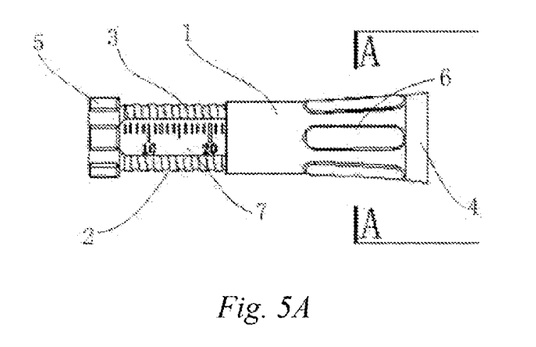
FIGS. 5A, 5B and 5C are respectively a perspective structural schematic diagram, a cross-sectional view of a front end of an elongation portion, and a cross-sectional view along AA of yet another example of the fluid flow metal sleeve involved in the second embodiment of the present disclosure.
Figure 5B:
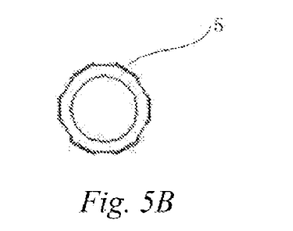
Figure 5C:
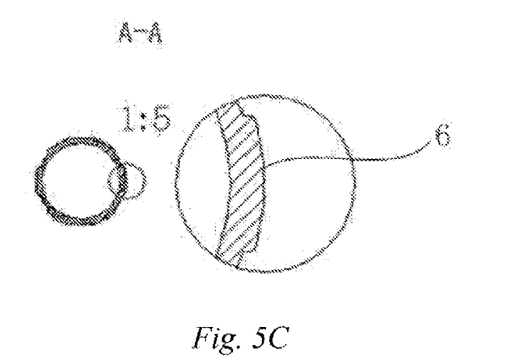

FIGS. 3A, 3B and 3C, FIGS. 4A, 4B and 4C and FIGS. 5A, 5B and 5C are perspective schematic diagrams and cross-sectional views of different examples of a fluid flow metal sleeve involved in a second embodiment of the present disclosure. As shown in FIGS. 3A, 3B and 3C, FIGS. 4A, 4B and 4C and FIGS. 5A, 5B and 5C, the periphery of the sleeve main body 1 is provided with sleeve main body slip-proof notches 6. The sleeve main body slip-proof notches 6 may be arc-shaped recessed notches, rectangular recessed notches, rectangular raised notches, or of other irregular shapes. The sleeve main body slip-proof notches 6 may be in a uniform or non-uniform distribution. FIGS. 3A, 3B and 3C respectively show a perspective structural schematic diagram of the fluid flow metal sleeve, with the elongation portion slip-proof notches and the sleeve main body slip-proof notches being arc-shaped slip-proof recessed notches, and cross-sectional views of the elongation portion slip-proof notches and the sleeve main body slip-proof notches. FIGS. 4A, 4B and 4C respectively show a perspective structural schematic diagram of the fluid flow metal sleeve, with the elongation portion slip-proof notches and the sleeve main body slip-proof notches being rectangular slip-proof recessed notches, and cross-sectional views of the elongation portion slip-proof notches and the sleeve main body slip-proof notches. FIGS. 5A, 5B and 5C respectively show a perspective structural schematic diagram of the fluid flow metal sleeve, with the elongation portion slip-proof notches and the sleeve main body slip-proof notches being rectangular slip-proof raised notches, and cross-sectional views of the elongation portion slip-proof notches and the sleeve main body slip-proof notches. The arrangement of the elongation portion slip-proof notches and the sleeve main body slip-proof notches can effectively enhance operability on length adjustment and holding and avoid the problems of slippage during use.

Figure 6:
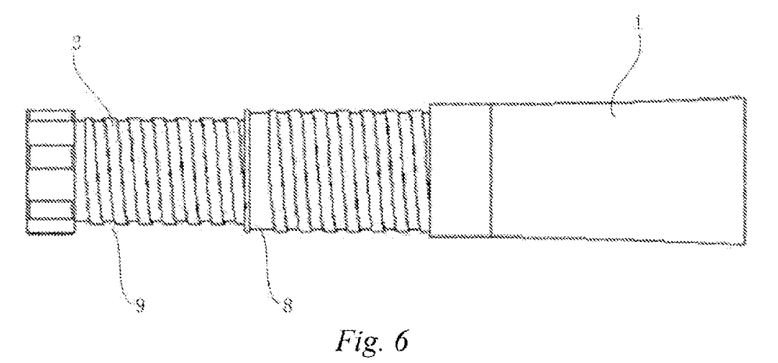
FIG. 6 is a perspective structural schematic diagram of a fluid flow metal sleeve involved in a third embodiment of the present disclosure.
Figure 7:
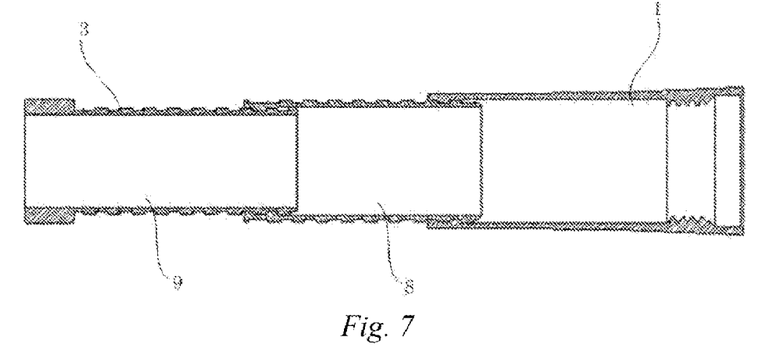
FIG. 7 is a cross-sectional structural schematic diagram of the fluid flow metal sleeve involved in the third embodiment of the present disclosure.

FIGS. 6 and 7 are respectively a perspective schematic diagram and a cross-sectional structural schematic diagram of the fluid flow metal sleeve involved in a third embodiment of the present disclosure. As shown in FIG. 6, the elongation portion of the fluid flow metal sleeve involved in the third embodiment of the present disclosure has two stages, including a first-stage elongation portion 8 and a second-stage elongation portion 9. Of course, the present disclosure is not limited thereto, and the elongation portion may be multi-stage. The use of the elongation portion of two or more stages increases the length adjustment range and improves the convenience and flexibility of operation. Furthermore, the inside of the elongation portion is provided with a limiting structure, such that each stage of elongation portion has a safety limit on the limit travel so as to prevent slippage during use, such that the device has high safety in use.

Figure 8:
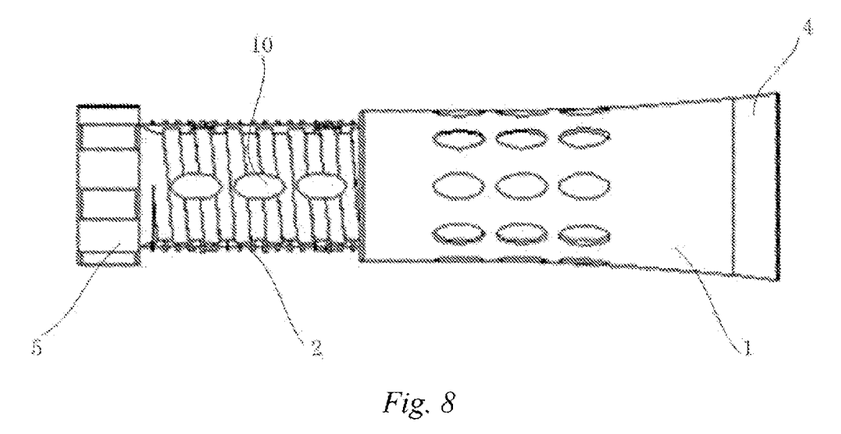
FIG. 8 is a perspective structural schematic diagram of an example of a fluid flow metal sleeve involved in a fourth embodiment of the present disclosure.
Figure 9:
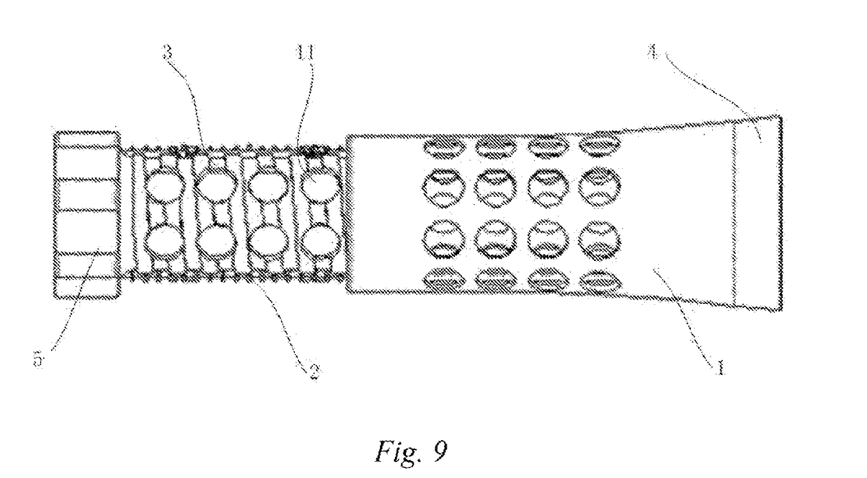
FIG. 9 is a perspective structural schematic diagram of another example of the fluid flow metal sleeve involved in the fourth embodiment of the present disclosure.
Figure 10:
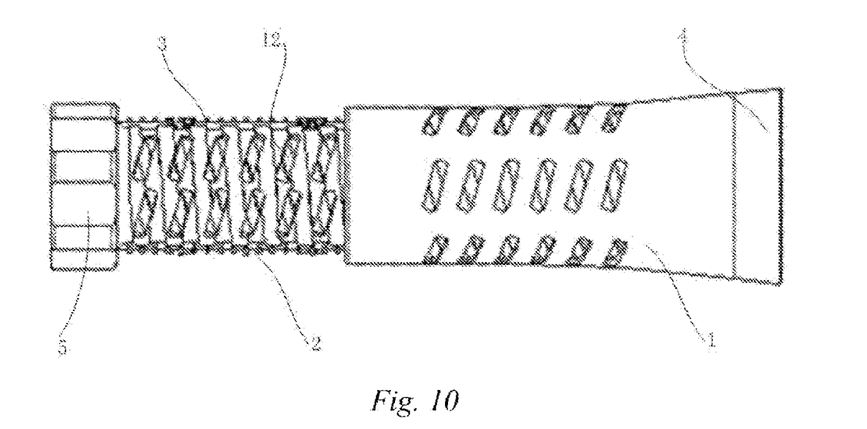
FIG. 10 is a perspective structural schematic diagram of yet another example of the fluid flow metal sleeve involved in the fourth embodiment of the present disclosure.

FIGS. 8 to 10 are perspective structural schematic diagrams of the fluid flow metal sleeve involved in a fourth embodiment of the present disclosure. As shown in FIGS. 8 to 10, the periphery of the sleeve main body 1 and the elongation portion 2 is provided with noise reduction notches of various shapes. In FIG. 8, the periphery of the sleeve main body 1 and the elongation portion 2 is provided with elliptical noise reduction notches 10. In FIG. 9, the periphery of the sleeve main body 1 and the elongation portion 2 is provided with circular noise reduction notches 11. In FIG. 10, the periphery of the sleeve main body 1 and the elongation portion 2 are provided with rectangular noise reduction notches 12. The noise reduction notches may also be of other regular or irregular shapes. The noise reduction notches may be of a through structure or a non-through structure, and may be in the uniform or non-uniform distributed. The arrangement of the noise reduction notches can prevent buzzing generated when the fluid passes through the fluid flow metal sleeve, thereby effectively reducing the noise decibels during incision. Meanwhile, the arrangement of the noise reduction notches can further reduce the weight of the fluid flow metal sleeve.

Finally, it should be noted that, the above embodiments are only for describing, but not limiting, the technical solutions of the present disclosure. Although the present disclosure have been described in detail with reference to the above embodiments, those of ordinary skill in the art should understood that the technical solutions stated in the above embodiments can still be modified, or some or all of the technical features therein can be equivalently substituted; and such modifications or substitutions do not make the essence of the corresponding technical solutions depart from the scope of the technical solutions of the embodiments of the present disclosure.

The invention claimed is:

1. A fluid flow metal sleeve, the fluid flow metal sleeve comprising:
   a sleeve main body and an elongation portion, which are of a hollow structure as a whole,
   wherein the sleeve main body is connected to the elongation portion by means of a threaded structure, a terminal end of the sleeve main body is connected to an ultrasound scalpel handle and enables an ultrasound scalpel to pass therethrough, and exterior distal peripheries of the sleeve main body and the elongation portion are provided with noise reduction notches,
   wherein the noise reduction notches are configured to reduce noise from the fluid flow metal sleeve, and
   wherein the noise reduction notches are of a non-through structure,
   wherein the elongation portion can be retracted into the sleeve main body.

2. The fluid flow metal sleeve according to claim 1, wherein the elongation portion has two or more stages.

3. The fluid flow metal sleeve according to claim 2, wherein an inside of the elongation portion comprising the two or more stages is provided with a limiting structure to prevent slippage of each stage of the elongation portion from the elongation portion.

4. The fluid flow metal sleeve according to claim 1, wherein a front end of a head of the elongation portion and the sleeve main body are provided with slip-proof notches, and an outer side of the elongation portion is provided with scale lines.

5. The fluid flow metal sleeve according to claim 4, wherein the slip-proof notches are arc-shaped recessed notches, rectangular recessed notches, rectangular raised notches, or of other irregular shapes.

6. The fluid flow metal sleeve according to claim 4, wherein the slip-proof notches are uniformly distributed.

7. The fluid flow metal sleeve according to claim 1, wherein an inside of the elongation portion is provided with a limiting structure to prevent slippage of the elongation portion from the sleeve main body.

8. The fluid flow metal sleeve according to claim 1, wherein the sleeve main body and the ultrasound scalpel handle are connected by means of a threaded structure, a snap-fitting structure, a top thread structure, an elastic expansion structure, a plugging structure, or a clamp slot structure.

9. The fluid flow metal sleeve according to claim 1, wherein the noise reduction notches are rectangular, circular, elliptical, or of an irregular shape.

10. The fluid flow metal sleeve according to claim 1, wherein the threaded structure has a cross-section in the shape of a rectangle, trapezoid or triangle.

11. The fluid flow metal sleeve according to claim 10, wherein the noise reduction notches are uniformly distributed.

* * * * *